(12) United States Patent
Pradere et al.

(10) Patent No.: US 8,785,852 B2
(45) Date of Patent: Jul. 22, 2014

(54) TERAHERTZ IMAGING DEVICE WITH IMPROVED THERMAL CONVERTER

(75) Inventors: Christophe Pradere, Villenave d'Ornon (FR); Jean-Christophe Batsale, Beguey (FR); Bruno Chassagne, Pessac (FR); Jean-Pascal Caumes, Bordeaux (FR)

(73) Assignees: Centre National de la Recherche Scientifique—CNRS, Paris (FR); Centre Technologique Alphanov Universite de Bordeau, Talence (FR)

( * ) Notice: Subject to any disclaimer, the term of this patent is extended or adjusted under 35 U.S.C. 154(b) by 483 days.

(21) Appl. No.: 13/262,497

(22) PCT Filed: Mar. 22, 2010

(86) PCT No.: PCT/FR2010/050516
§ 371 (c)(1), (2), (4) Date: Oct. 25, 2011

(87) PCT Pub. No.: WO2010/112730
PCT Pub. Date: Oct. 7, 2010

(65) Prior Publication Data
US 2012/0032082 A1 Feb. 9, 2012

(30) Foreign Application Priority Data

Apr. 1, 2009 (FR) .................................... 09 52097
Oct. 28, 2009 (FR) .................................... 09 57586

(51) Int. Cl.
*G01J 5/00* (2006.01)
*G01J 5/02* (2006.01)

(52) U.S. Cl.
USPC .................................... 250/338.1; 250/341.1

(58) Field of Classification Search
CPC ................. G01J 5/20; G01J 5/08; G01J 5/02; G01N 21/3581
USPC ........................................... 250/338.1, 341.1
See application file for complete search history.

(56) References Cited

U.S. PATENT DOCUMENTS 2,816,954 A 12/1957 Huffman
4,198,859 A 4/1980 Holtermann
(Continued)

FOREIGN PATENT DOCUMENTS

WO WO 99/62023 A1 12/1999
WO WO 00/09977 A1 2/2000
WO WO 2006/102181 A1 9/2006

OTHER PUBLICATIONS

French Search Report from corresponding French Patent Application No. FR 1050516 Report Dated May 31, 2010.
(Continued)

*Primary Examiner* — David Porta
*Assistant Examiner* — Mindy Vu
(74) *Attorney, Agent, or Firm* — Miller, Matthias & Hull LLP (57) ABSTRACT

The present invention relates to a terahertz imaging device comprising a terahertz source, a converter for converting terahertz radiation into thermal radiation, and a thermal detector. The converter has at least one zone sensitive to terahertz radiation, designed to absorb the terahertz radiation and vconvert the absorbed radiation into heat. This sensitive zone is close to a reference zone, of known absorption capacity, and the thermal detector is designed to measure the heat generated by the sensitive zone relative to the heat generated by the reference zone.

21 Claims, 8 Drawing Sheets

(56) References Cited

U.S. PATENT DOCUMENTS

| | | | |
|---|---|---|---|
| 4,965,448 A * | 10/1990 | Morse et al. | 250/252.1 |
| 7,564,567 B2 * | 7/2009 | Chen et al. | 356/502 |
| 7,692,147 B2 * | 4/2010 | Hu et al. | 250/336.1 |
| 2004/0263379 A1 | 12/2004 | Keller | |
| 2007/0145236 A1 * | 6/2007 | Kiesel et al. | 250/208.1 |
| 2008/0179519 A1 | 7/2008 | Andonian et al. | |

OTHER PUBLICATIONS

Kulipanov, G. N. et al., "Research Highlights from the Novosibirsk 400 W Average Power THz FEL", Terahertz Science and Technology, Jun. 26, 2008, pp. 116-117, figure 13.14, vol. 1, No. 2.

Malyutenko, V. et al., "UP-Conversion of Terahertz Radiation Induced by Photon Drag Effect", Physica E: Low-Dimensional Systems ad Nanostructures Jan. 2004 Elesevier NL, Jun. 6, 2003, pp. 563-566, vol. 20, No. 3-4.

Dobroiu, A. et al., "Terahertz Imaging System Based on a Backward-Wave Oscillator", Applied Optics, Oct. 20, 2004, pp. 5637-5646, vol. 43, No. 30, Optical Society of America.

Gregory, I. S. et al., "Continuous-Wave Terahertz System with a 60 dB Dynamic Range", Applied Physics Letters, May 13, 2005, American Institute of Physics.

Wei, A. et al., "Real-Time, Continuous-Wave Terahertz Imaging by Use of a Microbolometer Focal-Plane Array", Optics Letters, Oct. 1, 2005, pp. 2563-2565, vol. 30, No. 19, Optical Society of America.

Wu, Q. et al., "Two-Dimensional Electro-Optic Imaging of THz Beams", Applied Physics Letters, Jun. 11, 1996, pp. 1026-1028, American Institute of Physics.

Chan, W. L. et al., "Imaging with Terahertz Radiation", Reports on Progress in Physics, Jul. 12, 2007, pp. 1325-1379, IOP Publishing Ltd.

Cherkassky, V. S. et al., "Imaging Techniques for a High-Power THz Free Electron Laser", Nuclear Instruments and Methods in physics Research, Mar. 14, 2005, pp. 102-109, Elsevier.

Yang, J. et al., "Real-Time, Continuous-Wave Terahertz Imaging by a Pyroelectric Camera", Chinese Optics Letters, Jan. 10, 2008, pp. 29-31, vol. 6, No. 1.

Kasalynas, I. et al., "Design and Performance of a Room-Temperature Terahertz Detection Array for Real-Time Imaging", IEEE Journal of Selected Topics in Quantum Electronics, Mar./Apr. 2008, pp. 363-369, vol. 14, No. 2.

Dem'yanenko, M. A. et al., "Imaging with a 90frames/s Microbolometer Focal Plane Array and High-Power Terahertz Free Electron Laser", Applied Physics Letters, Apr. 3, 2008, American Institute of Physics.

Vinokurov, N. A. et al., "Visualization of Radiation from a High-Power Terahertz Free Electron Laser with a Thermosensitive Interferometer", Technical Physics, Aug. 23, 2006, pp. 911-919, vol. 52, No. 7, Pleiades Publishing, Ltd.

\* cited by examiner

TERAHERTZ IMAGING DEVICE WITH IMPROVED THERMAL CONVERTER

CROSS-REFERENCE TO RELATED APPLICATIONS

This application is a U.S. national stage filing of International Patent Application No. PCT/FR2010/050516 filed on Mar. 22, 2010, which claims priority under the Paris Convention to French Patent Application No. 09 52097, filed on Apr. 1, 2009 and French Patent Application No. 09 57586, filed on Oct. 28, 2009.

FIELD OF THE DISCLOSURE

The invention relates to the field of imaging, particularly for 2D real-time imaging applications in the spectral domain of terahertz waves.

BACKGROUND OF THE DISCLOSURE

The emergence of terahertz technology, with its wavelength range of about 3 mm to 30 µm, is generating significant industrial demand for sources such as pulsed lasers or continuous laser diodes, as well as imaging devices such as spectrometers, cameras, etc. Security, non-destructive testing, and research laboratory applications in particular are driving the development of high-performance terahertz imaging systems.

In response to such demand, terahertz imaging technologies are experiencing growth in two areas.

The first is in the growth of passive imaging systems, with measurement of ambient terahertz radiation. This is widely used in security. Whether for civil or military applications, or long-range vision in an opaque environment (smoke, fog, etc.), detection of weapons and prohibited products (in airports for example) has advanced the performance of cooled microbolometers for example.

The second is in a less advanced stage industrially, and concerns active imaging systems which make use of an external terahertz source. These are demonstrating growing potential in industrial applications. The contribution of spectroscopic analysis to imaging with femtosecond systems has become an important characteristic of the technology, with the development of pulsed laser sources covering a wide band of terahertz frequencies. This opens up a new range of applications for on-line non-destructive testing, although such imagers do not yet exist. In the laboratory, terahertz spectroscopic imaging exhibits the best sensitivity and the best dynamics. However, industrial applications are currently restrained by the fact that this type of imaging is achieved by scanning point by point (single-element detector), requiring a long acquisition time of several hours due to the length of the 2D scan to be performed and to the merging of the data to process the final image. The devices related to this technique are large and costly.

In order to exploit this potential, there has been significant activity in the development of a wide-band imaging camera with real-time data acquisition. A first commercial product exists that makes use of pyroelectric cameras, which are infrared motion detectors. The linearity, sensitivity and dynamics of pyroelectric cameras are not yet optimal for imaging, only for terahertz beam diagnostics.

The next generation of array detectors is currently still in the testing and development phase, primarily focusing on the use of thermal microbolometer cameras (sensitive within the 8-14 µm band) not yet adapted for the terahertz frequency domain.

Industrial and technological development of a real time terahertz imaging system is primarily limited today by the sensitivity and the signal-to-noise ratio (pyroelectric camera and microbolometer camera not being appropriate for the wavelength domain) for array detectors. The sensitivity can be increased using cryogenics, but the cost of obtaining a portable and compact system is high.

In another area of development, a first experimental attempt using a single-element thermal converter able to convert radiation into heat was conducted without success. The low sensitivity of the components used required high power terahertz sources (100 W) using a free-electron laser.

This type of technique is known, particularly from the document entitled "Visualization of Radiation from a High-Power Téra-hertz Free Electron Laser with a Thermosensitive Interferometer" by N. A. Vinoukorov et al., ISSN 1063-7842, Technical Physics, 2007, Vol. 52, no. 7, pages 911-919. This type of technique currently does not provide an absolute measurement, only a relative measurement of the radiation.

SUMMARY OF THE DISCLOSURE

One of the objects of the present invention is to provide a terahertz radiation analyzer, particularly for 2D real-time terahertz imaging applications at ambient temperature, with good detectivity for the spectral range in question. Another object of the invention is to propose a new type of thermal converter able to be used, for example, in the imager mentioned above.

The invention therefore proposes a terahertz analysis device, particularly for imaging applications, comprising:
   a terahertz source,
   a converter for converting terahertz radiation into thermal radiation, and
   a thermal detector,
with the converter comprising at least one zone sensitive to terahertz radiation, arranged to absorb the terahertz radiation and to convert the absorbed radiation into heat.

In the invention, said sensitive zone is in proximity to a reference zone of known absorption capacity, and the thermal detector is arranged to measure the heat generated by the sensitive zone relative to the heat generated by the reference zone.

The proposed analysis device is therefore relatively simple, passive (or active for a multispectral embodiment, as will be described below), and compact, and so is not as costly and is easy to produce industrially. The analysis device operates at ambient temperature, and permits real-time terahertz imaging aside from a very fast transient state due to the response time of the converter and therefore corresponding to its thermal inertia, which is just a few fractions of a second. This transient state can be taken into account by quantifying and calibrating it beforehand with a calibrated heat flow excitation. The response time for the thermal detector will be negligible considering the thermal inertia of the converter. The converter can be a product integrated with a standard infrared camera. In addition, having a zone sensitive to terahertz radiation in proximity to a reference zone allows obtaining an absolute temperature for the sensitive zone.

The thermal detector can be adapted to calculate, from said measurement, a temperature difference between the sensitive zone and the reference zone.

In certain embodiments, the heat generated by the reference zone is residual and the temperature difference is indicative of the power of the radiation received by the sensitive zone. If the reference zone absorbs virtually no radiation, one can assume that the increase in temperature in this zone is zero or is at least residual. In this case, simple comparison of the temperatures of the sensitive and reference zones indicates the intensity of the terahertz radiation received by the converter.

The converter may comprise a plurality of sensitive elements arranged in an array forming the sensitive zone and separated by boundaries forming the reference zone. The detector can be arranged to measure the heat generated by each sensitive element relative to the heat generated by the reference zone in order to determine a spatial distribution of the terahertz radiation on the converter.

The detector may comprise at least one infrared sensor, and the analysis device, particularly for imaging applications, then comprises an optical focusing means for focusing an infrared image from the converter on the infrared sensor. This allows using a simple infrared sensor to measure the heat of the sensitive zone relative to the reference zone.

In a sophisticated and particularly advantageous embodiment, the elements of the sensitive zone of the converter are arranged in an array and the detector can comprise a plurality of elements sensitive to infrared radiation, such as a camera with CCD (charge-coupled device), or preferably with microbolometer (sensor array sensitive to thermal radiation). Additionally or alternatively, as further detailed below, the detector may comprise at least one heat flow sensor, for example a flow meter based on the Peltier effect, to obtain an absolute value for the heat flow generated by the converter and, from this, an absolute value for the amount of terahertz radiation absorbed, transmitted, or reflected by an object illuminated by the terahertz radiation source. This flow meter can be coupled to said zone sensitive to terahertz radiation.

By using an infrared camera, the obtained infrared image is a digital image in which each element corresponds to a pixel in the image. It can be particularly advantageous to establish a correspondence between at least one element of an array detector and each sensitive element of the converter. Thus, for example, for each sensitive element of the converter there can be a corresponding pixel of an infrared image, or more than one pixel (4 or 9 pixels for example) in order to offer satisfactory image resolution from the converter.

Figure 2:
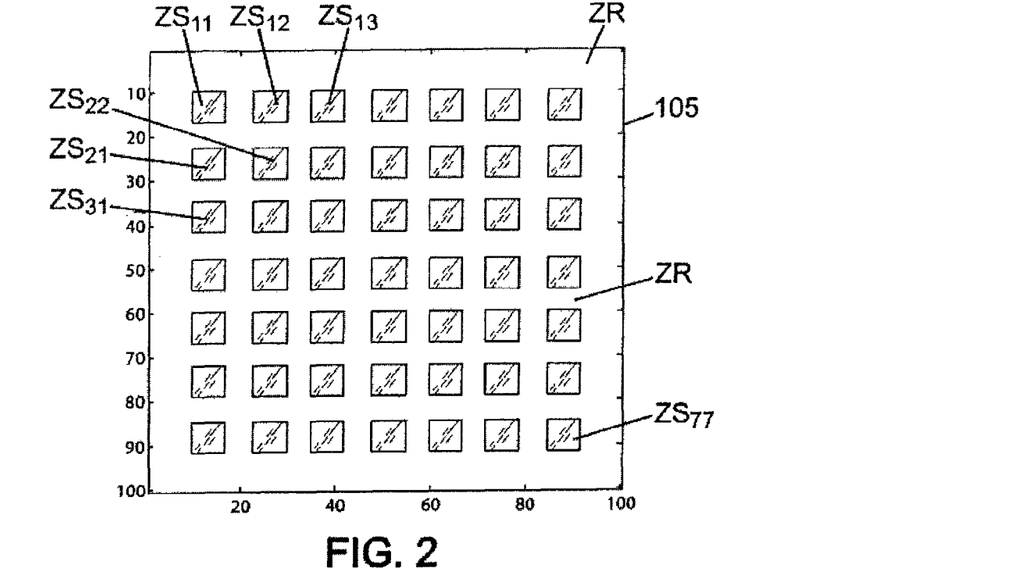
FIG. 2 illustrates a front view of a converter for converting terahertz radiation into thermal radiation according to an advantageous embodiment.

In such an embodiment, each sensitive element of the converter can be in the form of a cell of cubic or parallelipipedic dimensions equivalent to a wavelength typical of terahertz radiation (here on the order of several dozen microns to 1000 microns), for example on the order of 200 μm. Dimensions less than the maximum wavelength used, in this example less than 200 μm a side (in a plane parallel to the plane of the infrared image, as is shown in FIG. 2 discussed below) can be satisfactory. These 200 μm dimensions thus are explained relative to the value of the wavelength of the terahertz radiation and because of the Rayleigh criterion. Each sensitive element $ZS_{ij}$ (where i=1, 2, 3, . . . and j=1, 2, 3, . . . as illustrated in FIG. 2) is bordered by the reference zone ZR in which the terahertz power absorption is zero or residual.

The invention also relates to the converter itself, which converts terahertz radiation into thermal radiation and comprises for this purpose at least one zone sensitive to terahertz radiation, the sensitive zone being arranged to absorb the terahertz radiation and to convert the absorbed radiation into heat. In the invention, this sensitive zone is in proximity to a reference zone, of known absorption capacity, in order to measure the heat generated by the sensitive zone relative to the heat generated by the reference zone.

As indicated above, the converter can comprise a plurality of sensitive elements arranged in an array forming the sensitive zone, and separated by boundaries forming the reference zone. An array of N elements as represented in FIG. 2 allows obtaining an advantageous spatial resolution and a reduction in the inter-element crosstalk.

The sensitive zone may comprise a material in which the terahertz absorption is a function of the wavelength of the terahertz radiation. This allows varying/adapting the absorption capacity of the sensitive zone to the frequency of the terahertz radiation. In this "multispectral" application, the converter is active. Each sensitive element (in the form of a cell) can comprise several respective circuits holding various terasensitive materials sensitive to different terahertz frequencies. These are referred to as "microfluidic channels", which will be further described below. This effect is advantageous in certain applications, for example if a high absorption capacity is required.

The sensitive zone can contain at least water, glass, and/or carbon nanotubes, as compounds particularly sensitive to terahertz radiation. The choice of materials used will thus have an effect on the absorption capacity of the sensitive zone.

In the channel application mentioned above, the sensitive zone can contain at least two terasensitive liquids which can be interchanged by channel means (systems of microfluidic channels) in order to be exposed to the terahertz radiation in the proportions chosen. The sensitive zone (or each element of the sensitive zone) and the reference zone (which can border these elements) are adjoining. This allows obtaining a compact converter and a good contrast for evaluating the radiation intensity at each sensitive element relative to a reference.

In addition, it is possible to insert a heat insulating layer in the converter, between the sensitive zone and the reference zone, in order to reduce the heat losses from the sensitive zone.

The invention also concerns a method for terahertz analysis, particularly for imaging applications, wherein there is a converter for converting terahertz radiation into thermal radiation, comprising at least one zone sensitive to terahertz radiation and arranged to absorb the terahertz radiation and convert the absorbed radiation into heat. In the invention, this sensitive zone is in proximity to a reference zone of known absorption capacity, and the heat generated by the sensitive zone is then measured relative to the heat generated by the reference zone in order to determine the terahertz power received by the converter.

As indicated above, the converter can comprise a plurality of sensitive elements arranged in an array forming the sensitive zone, and separated by boundaries forming the reference zone, and the heat generated by each sensitive element can then be measured relative to the heat generated by the reference zone in order to determine a spatial distribution of the terahertz radiation on the converter.

In one application in baggage security, an object, for example a purse, can be placed in the path of terahertz radiation of a given power between a source of terahertz radiation and the converter; and a spatial distribution of the power of the terahertz radiation received at the converter is determined. This enables effective non-destructive testing of objects.

One can also determine a first spatial distribution of the power of the terahertz radiation received at the converter, without placing an object in the path of the radiation, and determine a second spatial distribution of the power of the terahertz radiation received with the object then placed in the path of the radiation. The first distribution, for calibration, can then be compared to the second distribution. Here, placement of the object in the path of the radiation also means:
- the converter receives the transmitted terahertz radiation which the object allows to pass through (in this configuration, the terahertz source and the converter are placed on opposite sides of the object to be analyzed and/or imaged),
- the converter receives reflected terahertz radiation which the object reflects towards the converter (in this configuration, the terahertz source and the converter are placed on the same side of the converter).

The sensitive zone can comprise a material in which the terahertz absorption is a function of the wavelength, and the above steps are applied while varying the wavelength to obtain a mapping of the object as a function of both the power of the radiation and the wavelength.

The invention has applications in non-destructive testing, in surveillance, and in real-time imaging in an opaque medium. This technology can be substituted for or can supplement certain tests that use x-ray radiography, offering the benefit of non-ionizing radiation (unlike X-rays).

BRIEF DESCRIPTION OF THE DRAWINGS

Other features and advantages of the invention will become apparent from the following detailed description and the attached drawings, in which.

DETAILED DESCRIPTION OF THE DISCLOSURE

Figure 1:
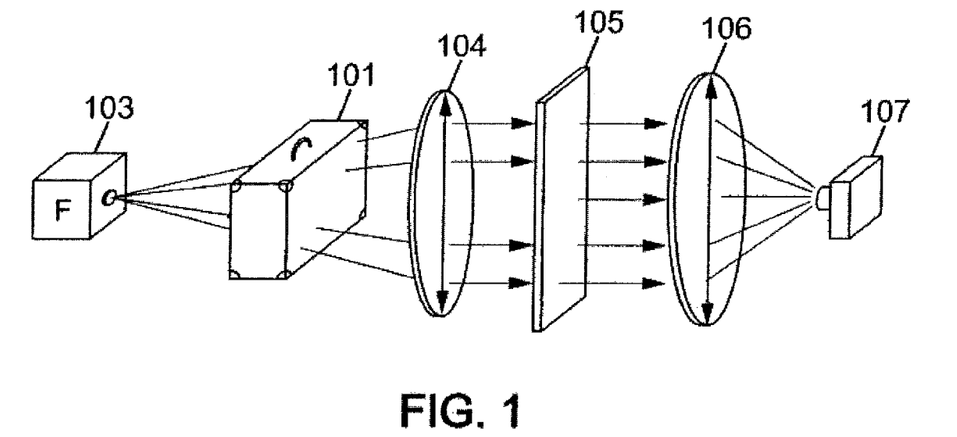
FIG. 1 illustrates an example of using a system of the invention to obtain an image representing the content of an object to be imaged.

Different embodiments of the invention are now detailed with reference to these figures. A first embodiment concerns a 2D real-time array imaging device for the far infrared spectral domain. FIG. 1 illustrates a configuration for the non-destructive testing of an object 101, such as a suitcase 101, for an application related to airport passenger security.

A terahertz source or emitter 103 emits electromagnetic waves within the spectral domain of terahertz waves, which then at least partially traverse the object 101. FIG. 1 also shows a lens 104 that directs the terahertz radiation traversing the object to be imaged onto a thermal converter in the sense of the invention. The converter in the example described is in the form of a transducer plate 105 placed in front of or integrated into an infrared imaging device, such as an objective 106, installed in front of a thermal detector (for example an infrared thermographic camera 107). The lens 104 can be of Teflon for example, as this material is transparent to terahertz radiation and is easy to machine. The converter 105 is placed in a position substantially transverse to the path of the radiation. The thermal converter 105 receives the electromagnetic waves radiated by the source 103 and traversing the object 101. The thermal converter 105 converts the terahertz electromagnetic waves into heat as is explained in more detail below.

The objective 106 applies a certain enlargement in order to maintain a satisfactory spatial resolution while providing an image of the plane of the thermal converter 105 on a thermal detector which may or may not be array-based (camera 107). This objective 106 can be the focusing objective for the camera 107. The thermographic camera 107 delivers a digital image (in pixels) of good spatial resolution and which allows precise measurement of a temperature increase induced by the terahertz radiation striking the heat converter 105.

The heat converter 105, the objective 106, and the detector 107 together form a new type of terahertz imager. This terahertz imager, operating at room temperature, enables real-time 2D imaging in the spectral domain of terahertz waves by the simple addition of a thermal converter 105 sensitive to terahertz radiation (or "tera-sensitive") in front of the objective 106 of the detector 107. As a result, this proposed simple addition allows a same camera to have a 2D imager either in the thermal infrared or in the terahertz domain. This new spectral domain (the very far infrared, meaning wavelengths>12 μm, which means frequencies<25 THz) is still very new in terms of thermal imaging. The real-time 2D imagers currently on the market are not as flexible as the imager of the invention, for the spectral domains concerned.

This type of terahertz imager can therefore be completely integrated. In particular, the converter 105 can be integrated with the objective 106. This integration may simply be a mechanical coupling. In a more sophisticated embodiment, as carbon nanotubes have very good terahertz radiation absorption properties, carbon nanotubes can be deposited directly on a surface of the objective 106 and through a grid in order to separate the elements $ZS_{ij}$ of the zone sensitive to the terahertz radiation.

The configuration illustrated in FIG. 1 operates during transmission, with the elements 105, 106 and 107 being placed behind the object to be imaged 101. In this case, if the object (a suitcase, for example) contains a pattern to be detected which reflects or absorbs terahertz radiation, such as a metal weapon, the converter does not receive radiation in a zone of its surface due to the "shadow effect", and this zone then illustrates the pattern to be detected. One can also consider an assembly based on reflection to the converter. In this alternative, the elements 105, 106 and 107 are placed on the same side as the source 103 and the converter 105 receives the radiation reflected by the weapon.

For certain applications, it is also possible for the objects to be imaged in the terahertz domain to be directly coupled to the converter 105.

Two embodiments of the converter 105 are described below:
- a non-adiabatic converter (where the sensitive zone is not thermally isolated from the reference zone) and
- an isoperibol or adiabatic converter (with no coupling between the sensitive zone and the reference zone).

In both cases, the converter remains terasensitive. Only the thermal sensitivity (increase in temperature, heat diffusion) changes.

FIG. 2 illustrates in more detail the structure of the converter 105 in the first embodiment (a non-adiabatic converter). The converter 105 comprises zones $ZS_{11}$, $ZS_{12}$, $ZS_{21}$, $ZS_{22}$, $ZS_{31}$, ... (designated below as $ZS_{ij}$ where i,j=1, 2, 3, ...) sensitive to terahertz radiation, which are surrounded by the reference zone. These sensitive zones $ZS_{ij}$ are able to convert the terahertz radiation into thermal radiation. FIG. 2 also shows a horizontal and vertical scale. This scale is used in FIGS. 3 to 7 to facilitate comparison of these figures.

The sensitive zones can be cells enclosing a solid, liquid, or gas. The cells are delimited at least on the side exposed to the terahertz radiation by a wall transparent to terahertz radiation (for example of Teflon). A material transparent to thermal radiation can be used on the other side of the converter, to delimit the cells on the other face of the converter.

The terasensitive material inside the cells may be or may contain water, glass, or carbon nanotubes. The carbon nanotubes are of very hard and strong materials and also have a remarkably high electrical and/or thermal conductivity. These tera-absorbent materials, especially when they are liquid, can be quickly changed or modified, using systems of microfluidic channels. The sensitive zones can therefore contain at least two terasensitive liquids which can be interchanged by channel means to achieve exposure at least in alternation to terahertz radiation or exposed at the same time to the radiation but in respective chosen proportions. The increase in temperature of the thermal converter 105 is proportional to the amount of terahertz heat flow received. The sensitivity of the overall system then depends on the absorption efficiency of the material in the cells, within the terahertz spectral range.

In the case of a non-adiabatic converter, the material is not thermally insulated from a reference zone. In FIG. 2, the white squares (having slight reflections to illustrate the transparency of the Teflon wall to terahertz radiation) represent the absorption zones $ZS_{ij}$ adjoining the reference zone ZR, here with no separation by thermal insulation. In this embodiment, the reference zone is of metal, for example steel, which reflects terahertz waves. The reference zone is therefore not sensitive to the terahertz radiation in this embodiment. One can say that this reference zone has a known absorption value, as this value is zero (or at least residual). The absorption value of the reference zone is, in any case, lower than the absorption value of the sensitive zone.

Only the terasensitive portion will absorb this heat flow. In FIG. 2, this radiation-sensitive portion is represented as a matrix of N (N≥1) elements or "pixels". A matrix of N pixels enables pixelation (preferred spatial resolution) and reduction of interpixel crosstalk. The size of a pixel is proportional to the wavelength used. As a result, the size of a pixel is for example within the range 50 μm-500 μm (100 μm typically corresponding to 3 THz). Advantageously, a pixel of the image obtained by the thermal camera 107 consists of 3×3 pixels of a converter 105 when it concerns a thermal camera providing a digital image. It is also possible to envisage other possibilities to the extent that a pixel of the obtained image consists of at least one pixel of the converter 105.

As a variant, it is possible to have an embodiment in which the reference zone is sensitive to radiation. However, the absorption capacity of the reference zone would then have to be well known as a function of the incident radiation. This embodiment still permits an absolute measurement in the sensitive zone.

Figure 3:
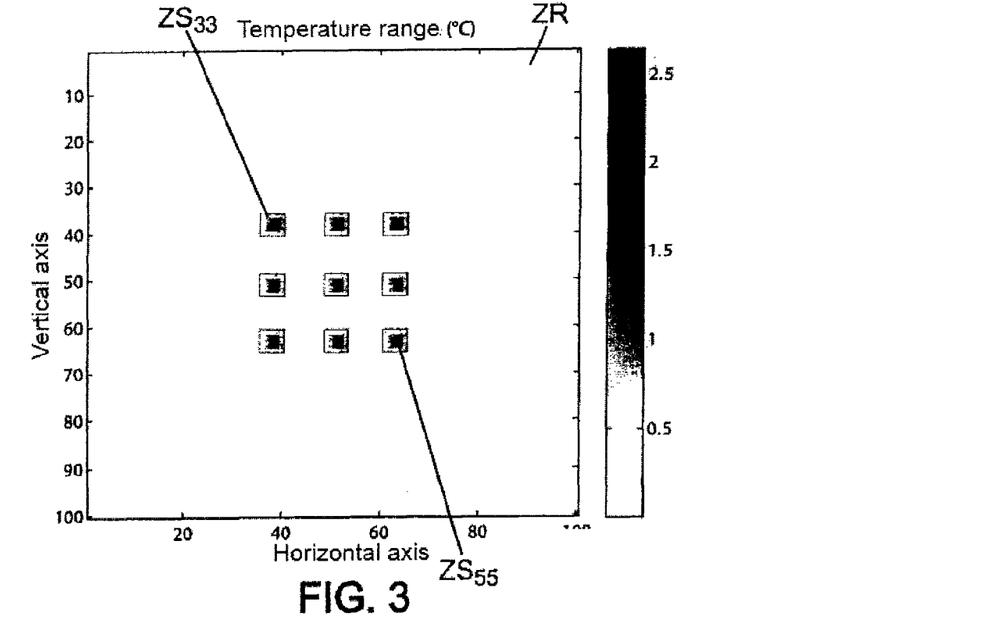
FIG. 3 illustrates a front view of the converter of FIG. 2, during operation.
Figure 4:
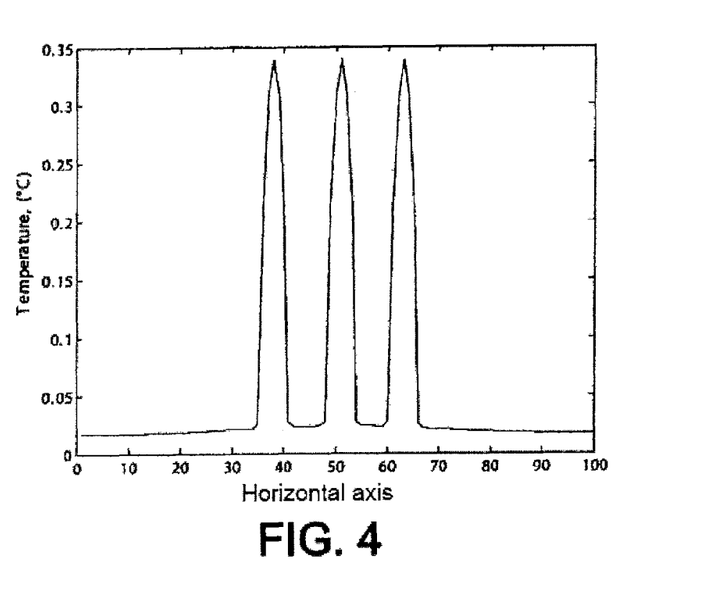
FIG. 4 illustrates a temperature profile for the converter of FIG. 2, during operation.

This absorption by the sensitive zone generates an increase in temperature as illustrated by FIGS. 3 and 4. FIG. 3 shows a front view of the converter 105 as seen by the thermal imaging camera 107. The scale shown in this figure illustrates the various temperature differences in degrees Celsius. The white color corresponds to a small increase and the dark gray corresponds to a large increase. The result shown is from a 2D thermal simulation of the temperature range obtained when a heat flow (thermal source) is applied to the pixels situated at the center of the array of the converter 105. Note the detection of a higher temperature, relative to the rest of the converter 105, at the nine central elements in the example represented. The reference zone and the sensitive elements not irradiated therefore remain relatively cool. One will also note that the sensitive elements become progressively hotter towards the center of the converter.

FIG. 4 shows an average temperature profile on the y axis. The increase in temperature in the reference zone is residual, approaching zero degrees. In practice, the temperature range observed corresponds to the range measured by the infrared camera. One will note the sharpness and height of the peaks compared to the background noise.

Various shapes and sizes for the profiles of the absorbent/reflective elements are possible, depending on the spatial resolution desired. The absorption zones can, for example, be in the form of squares, round zones, straight bands in directions which can vary between horizontal and vertical bands, circular bands, etc. The resolution of the image obtained can be improved by decreasing the size of the individual absorption zones. However, a reference zone is provided of sufficient dimensions to obtain a still or moving image which illustrates the content of the object to be imaged, at a satisfactory resolution.

Figure 5:
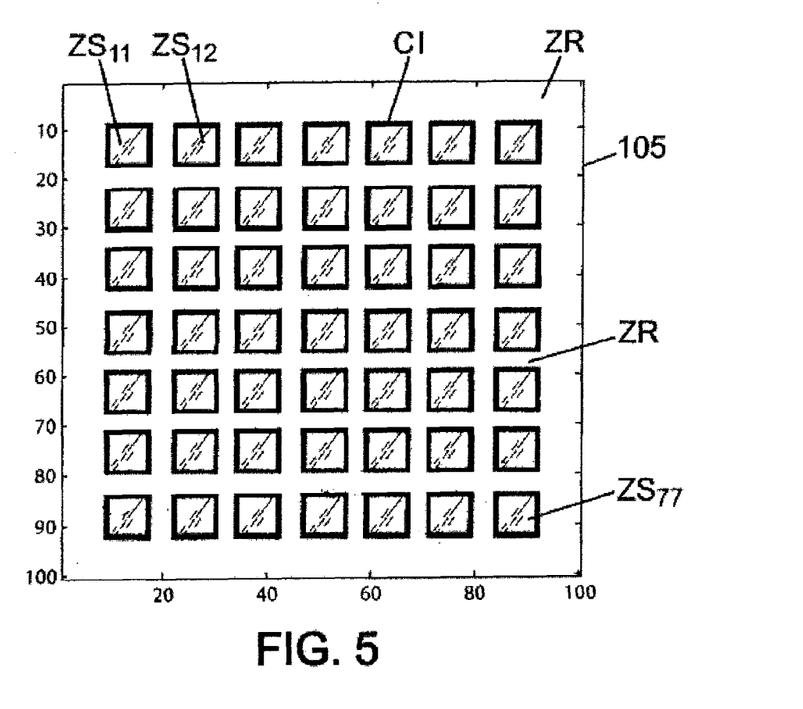
FIG. 5 illustrates a front view of another converter for converting terahertz radiation into thermal radiation according to another embodiment.

The second embodiment, the case of an isoperibol converter, is illustrated in FIG. 5. Here, a heat insulating layer CI (transparent to terahertz waves) is inserted between the sensitive zones and the reference zone. This insulating layer acts in particular on the thermal behavior of the converter 105.

Figure 6:
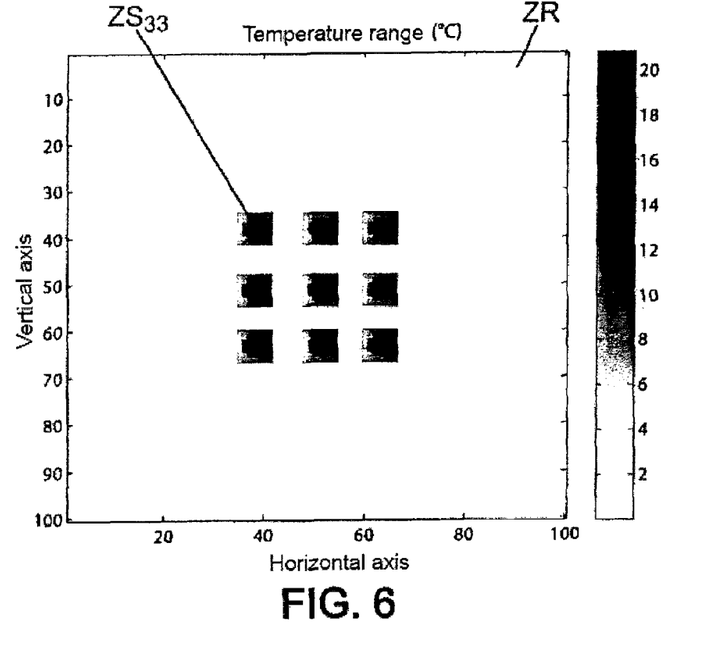
FIG. 6 illustrates a front view of the converter of FIG. 5, during operation.
Figure 7:
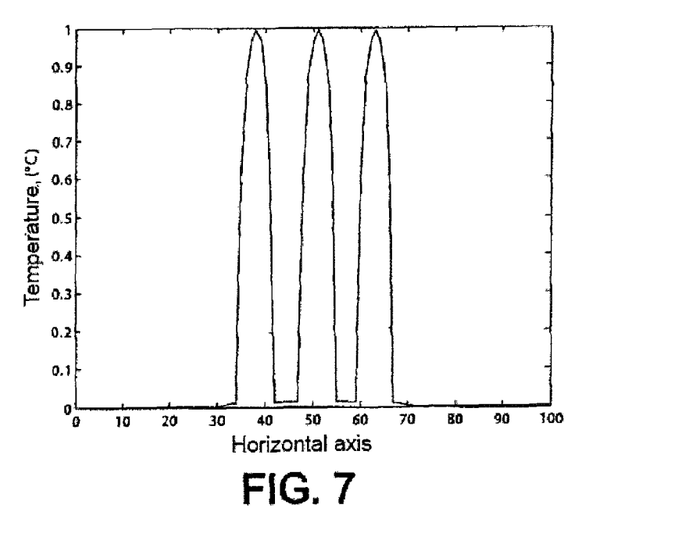
FIG. 7 illustrates a temperature profile for the converter of FIG. 5, during operation.

FIGS. 6 and 7 show the simulation results for the isoperibol converter, while FIGS. 4 and 5 show the results of the same 2D thermal simulation with the non-adiabatic converter. Note that the temperature scale is not the same in FIG. 6 as in FIG. 3. One will also note the excellent ratio of peak height to background noise in FIG. 7.

Depending on the type of application, it will be preferable to use one or the other of the embodiments. In the case of an isoperibol converter (FIG. 7), the temperature increase is clearly greater than the temperature increase in the non-adiabatic converter (FIG. 4). Of course, the heat losses are lower in the isoperibol converter and are better controlled (simple thermal resistance between the sensitive element and the reference zone).

The contrast between the reference zone and the sensitive zone determines the signal-to-noise ratio of an infrared image (still or video). As indicated above, the reference zone formed by a grid of N pixels (N≥1) obtains an advantageous spatial resolution. This grid can also have the function of reflecting the terahertz radiation (in an assembly other than the one represented in FIG. 1), thus delimiting the boundaries of the pixels. Inter-pixel crosstalk is effectively eliminated if the material of the grid is also a good heat conductor. In fact, this allows a relative temperature measurement between the grid (reference temperature) and the absorbent element. This type of technology is perfectly suited for detectors of large dimensions, since traditional thermographic imagers allow observing large fields with a good spatial resolution. One can also accurately measure the temperature of the reference grid by using a contact temperature sensor, for example a platinum probe. As one can see, the invention presented above is open to multiple variants, depending on the intended applications.

Figure 8:
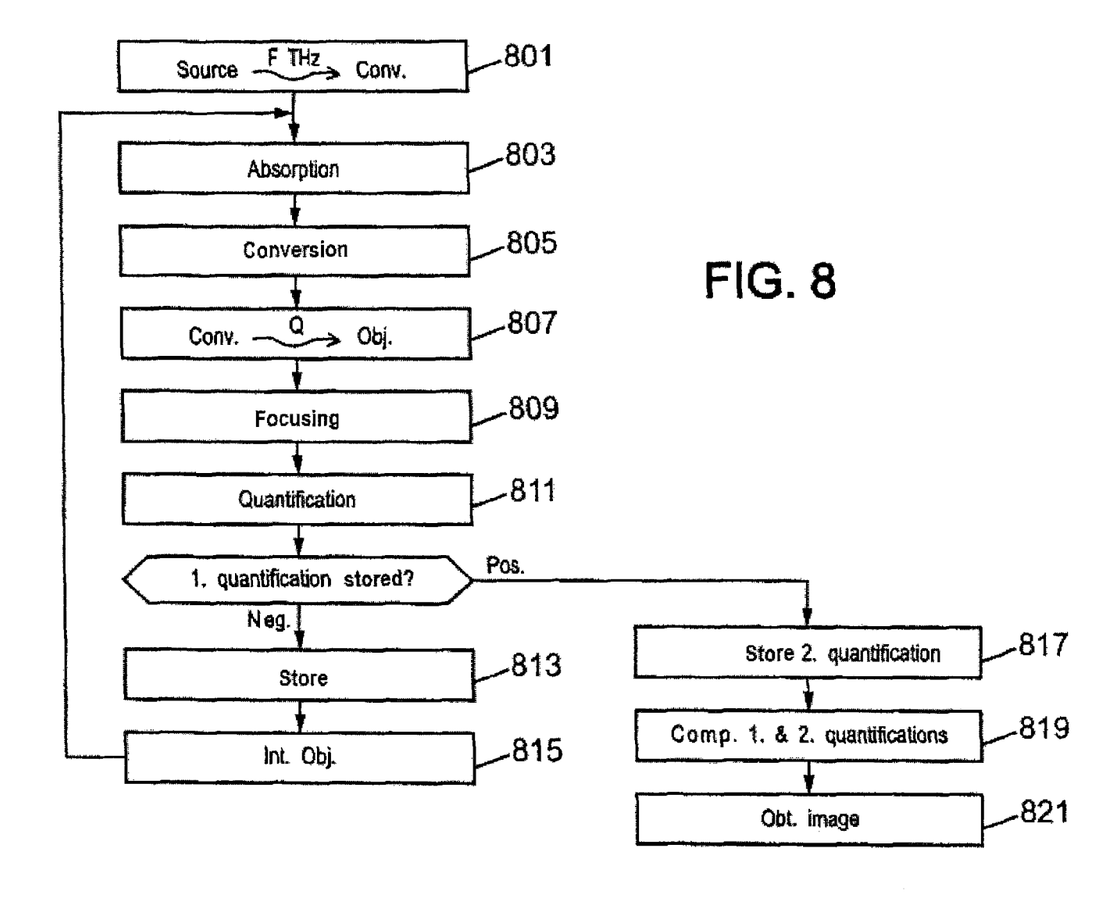
FIG. 8 illustrates a flowchart for a method for imaging the content of an object according to one embodiment.

One embodiment of the method for obtaining the image representing the content of the object to be imaged is illustrated in the flowchart in FIG. 8. In step 801, the emitter 103 emits terahertz radiation in the direction of the thermal converter 105. The absorption zones of the thermal converter 105 absorb the radiation received (step 803), particularly in the terahertz wavelengths. In step 805, under the effect of the absorbed terahertz radiation, the temperature of this thermal converter 105 (terahertz/IR converter) rises by an amount proportional to the terahertz radiation received. A steady state is reached for the temperature increase. In step 807 this thermal converter 105 re-emits thermal radiation Q according to the law of thermodynamics for black bodies. This radiation can be measured or captured by the thermal detector 107, via an objective 106, which, in step 809, directs the thermal radiation towards the detector 107. In step 811, the thermal detector 107 quantifies the thermal radiation received at the detector. This allows determining both the power of the terahertz wave received at the converter and its spatial representation.

If the result of the first quantification is not yet stored, in step 813 the detector 107 stores the result of the quantification. After storing the first quantification, an object is introduced in front of the thermal converter 105 in step 815. As a result, the radiation passes through the object and the method continues in step 803.

On the other hand, if the result of the first quantification has already been stored, in step 817 the result of a second quantification is stored, obtained when the radiation passes through the object 101. In step 819, the results of the first and second quantifications are compared. Based on this comparison, an image representing the content of the object 101 is obtained in step 821.

Note that it is not necessary to obtain a quantification conducted without the object. To obtain an image, it is sufficient to perform the quantification by placing an object directly in front of the converter 105 without necessarily conducting a reference quantification. One can appreciate the role that the reference zone of the converter plays here, as it allows doing without a first reference quantification.

These examples have illustrated the feasibility and validity of an array of terasensitive thermal converters. Several applications can be considered on this basis. First, two thermal configurations are possible, non-adiabatic or isoperibol depending on the sensitivity desired. In each case, an absolute radiation power is accessible via the detector 107. This radiation power results from the difference between the average temperature of a sensitive element and that of the reference zone that surrounds it, with a greater advantage in the isoperibol case where the heat losses between the sensitive element and the reference zone are completely controlled by means of simple thermal resistance due to the intervening insulation. By these measures, it is possible to quantify the terahertz flux arriving at the detector, which allows determining both the power of the terahertz wave and its spatial representation.

Because of this advantage, it is possible to create a camera adapted for terahertz imaging, by evaluating the transmission through or reflection from an object placed in the terahertz field, in particular by calculating the difference between the initial temperature distribution measured at the converter 105 (without an object to image) and that obtained when the object is placed in the field.

A variant of using the device of the invention in terahertz imaging can also be envisaged as described below. This is more generally an application to terahertz analysis, with a quantitative, absolute measurement of the terahertz radiation received by the converter.

Thus, in another embodiment, the infrared camera is replaced by a solid sensor which is a heat flow meter, associated with the converter described above, to provide an absolute measurement of the terahertz flux absorbed by the converter. Such an embodiment offers the particular advantage of being both more economical and more sensitive than the use of an infrared camera. The sensitivity of an infrared camera is on the order of 2000 µW, compared to 10 µW for a heat flow meter based on the Peltier effect.

Figure 9A:
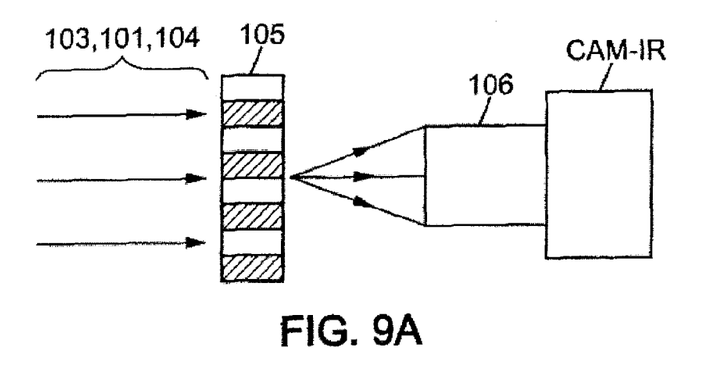
Figure 9B:
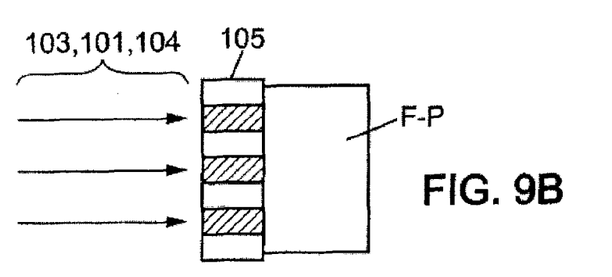
FIG. 9B illustrates an arrangement of a terahertz analysis device using a Peltier effect-based flow meter for the heat flow sensor as a variant of an infrared camera, for comparison with FIG. 9A which represents an imaging device using a camera, FIGS. 10A and 10B schematically represent a heat flow sensor which is a Peltier effect-based flow meter coupled with a thermal converter, from the front and side respectively.

In this embodiment, as represented in FIG. 9B (for comparison with FIG. 9A and having a diagram equivalent to the one in FIG. 1 discussed above), the primary difference from the embodiment presented above and represented in FIG. 9A (in which the designation CAM-IR denotes an infrared camera) lies in the type of heat sensor 107, at the output from the converter 105 in FIG. 1. In fact, in this new embodiment, the infrared camera assembly is replaced with a heat flow meter, for example one based on the Peltier effect, and is denoted F-P in FIG. 9B. The advantage of such an embodiment is the detection sensitivity, as it is able to measure a terahertz flux 1000 times lower than what the infrared camera can measure, as shown below.

Figure 10A:
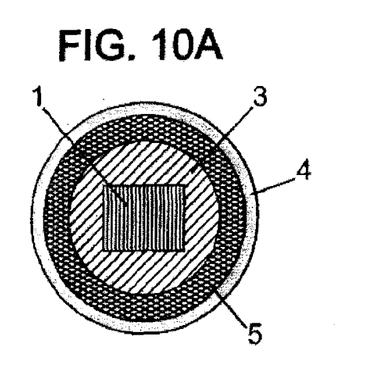
Figure 10B:
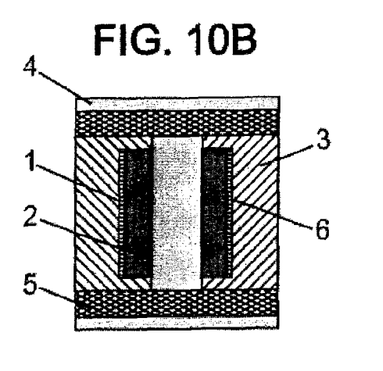

FIGS. 10A and 10B illustrate an exemplary embodiment of such an infrared flux sensor based on the Peltier effect, combined with a terahertz/infrared radiation thermal converter in the sense of the invention. In these figures, 1 denotes the thermal converter, 2 (in FIG. 10B corresponding to a cross-sectional profile view) denotes the flow meter itself, arranged to generate an electrical voltage as a function of an injected heat flow (in watts), by thermoelectric effect. The reference 6 in FIG. 10B denotes an electrical heating resistor for calibration.

A flow meter based on the Peltier effect generally operates under the principle in which a temperature difference at the terminals of the flow meter (at the thermal converter 2 and resistor 6) is then converted into electric current, for which a voltage is measured for example. In the exemplary embodiment here, a temperature is set in the flow meter in proximity to the resistor 6, which serves to keep this temperature constant, and then the exact heat flow that the thermal converter 1 receives is measured as an absolute value, quantitatively and not relatively.

Still with reference to FIGS. 10A and 10B, the thermal converter 1 is again surrounded, as described above, with thermal insulation 3, preferably transparent to the domain of terahertz frequencies, in a manner that ensures that the entire heat flow collected downstream from the thermal converter 1 originates from the thermal converter 1 alone. The assembly is further isolated thermally by an insulating casing 5. A metal frame 4, which is isothermal, encloses these various elements to contribute its properties of thermal inertia.

Figure 11:
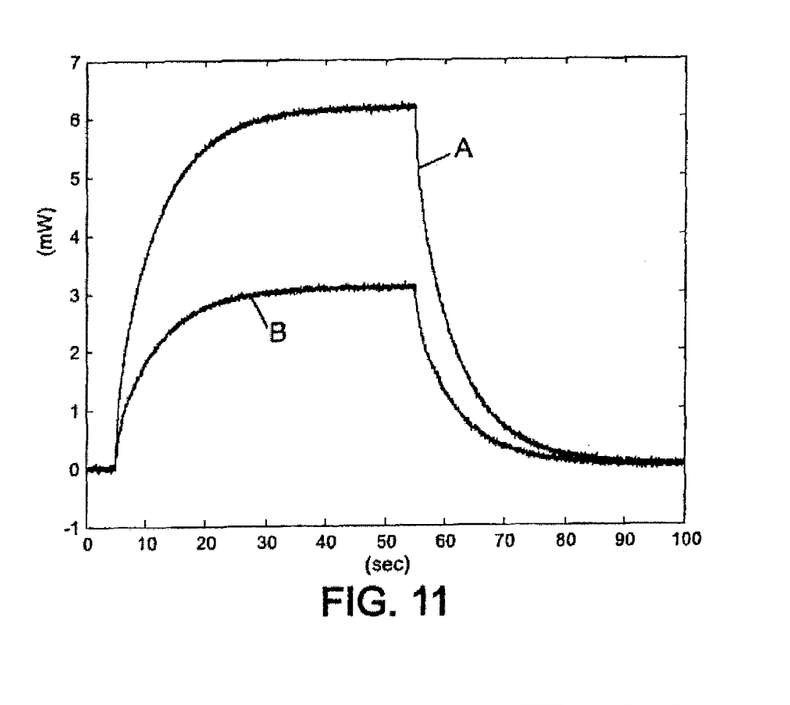
FIG. 11 represents the variation over time of the heat flow as measured by the Peltier effect-based flow meter, in the case where the terahertz radiation directly strikes the converter (curve A), and in the case where an item is placed between the terahertz source and the converter (curve B)

Tests conducted with such a configuration do indeed show that the exact heat flow received by the thermal converter 1 is quantitatively measured as an absolute value. In FIG. 11, the variation over time of the power in milliwatts (mW) of the heat flow measured by the Peltier effect-based flow meter is represented:

in curve A, for terahertz radiation directly issuing from a terahertz source, with no object placed between the source and the thermal converter 1, and in curve B, by placing between the source and the thermal converter 1 a material such as a carbon sheet for which the absorption of the terahertz flux is known to be 50%.

One will note that the power measured for curve B reaches, after stabilization over time, exactly half of what it reaches for curve A. It is therefore possible to measure any power issuing from a terahertz beam, using the flow meter. The terahertz beam directly issuing from the source is then sent to the thermal converter 1. The transient change in the flow over time is then obtained (curve A in FIG. 11). By determining the difference between the initial flow and the final flow (steady state), the incident flow delivered by the terahertz source is obtained. It is then sufficient to insert an object to be imaged in order to deduce its absorption.

Figure 12:
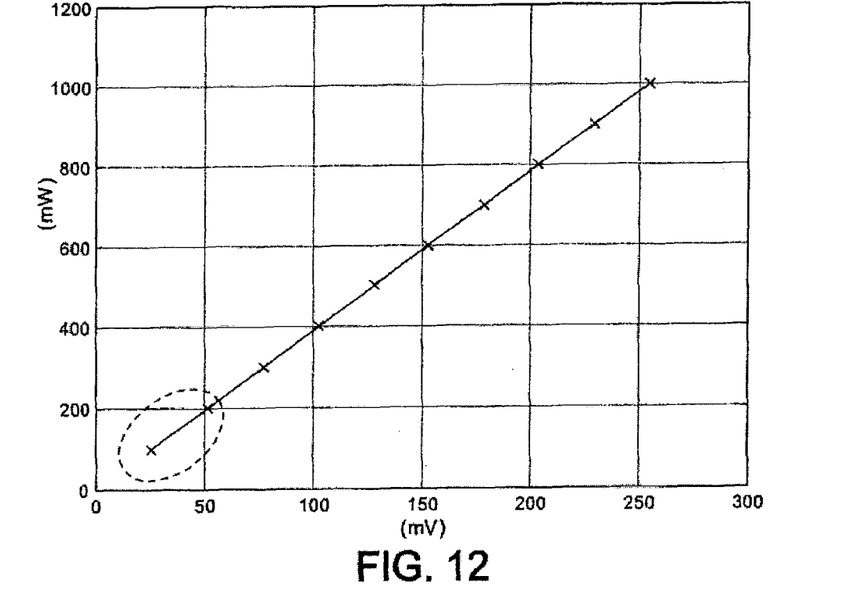
FIG. 12 represents an electrical calibration curve for the heat flow sensor.

However, one precaution to be taken consists of properly calibrating the flow meter. For this purpose, the electrical resistor 6 is used to inject different wattages into the flow meter-converter assembly. Then the resulting voltage is measured at the terminals of the flow meter. With reference to FIG. 12, this voltage measured as a function of the injected wattage is graphed, to observe a linear variation and determine a calibration coefficient in volts per watts (V/W), for a given flow meter. Typically, this coefficient can vary from one flow meter to another by 0.25 to 1 V/W.

Figure 13:
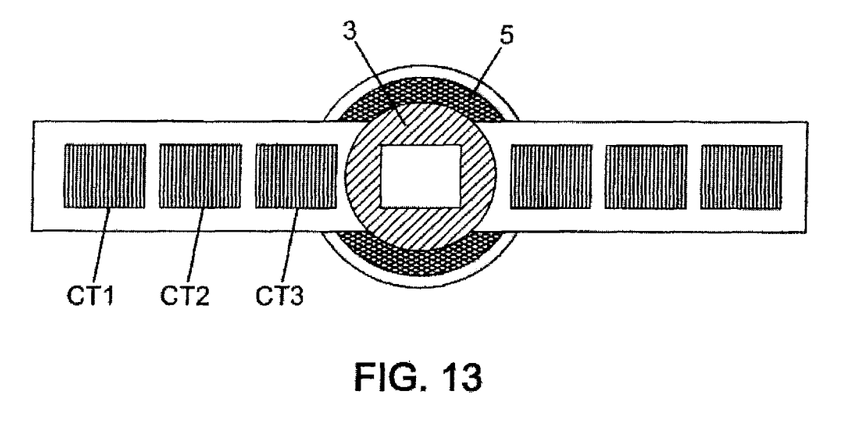
FIG. 13 is a diagram of a multi-spectral sensor using a plurality of thermal converters CT1, CT2, CT3, sensitive to different wavelengths of terahertz radiation.

As one will observe in FIG. 12, it is possible to measure extremely weak terahertz fluxes (region encircled by a dotted line). In practice, fluxes on the order of ten nanowatts can be measured, which should allow the use of terahertz sources having femtosecond pulses. Similarly, it is possible to place a filter wheel or an element for advancing different thermal converters CT1, CT2, CT3, . . . , in order to obtain a multi-spectral sensor as represented in FIG. 13. An improvement can also be expected in the thermal inertia of the flow meters (currently on the order of a few tens of seconds to reach a steady state).

It is possible to have individual flow meters for each element $ZS_{ij}$ of the converter of FIG. 2 or FIG. 5. In this case, there can be a plurality of flow meters for example, each several centimeters in diameter and each associated with an element $ZS_{ij}$ (or with a group of several adjacent elements $ZS_{ij}$). As a variant, it is also possible to have a single flow meter of larger dimensions (for example a few tens of centimeters) and to measure an average heat flow for all the elements of the converter 105. This embodiment allows, for example, precisely measuring the amount of terahertz radiation absorbed by an object placed between the source and the converter (for analysis of a powder, for example of carbon nanotubes, in order to determine the percentage of nanotubes or other characteristic). Thus, in such an application, a wide range of uses can be anticipated such as analysis (characterization) by terahertz beam (power, spatial distribution), measuring the transmission of a material in the terahertz domain, or other applications.

It is also possible to implement imaging applications based on a single flow meter. In fact, the terahertz beam can be aligned to aim towards an object to be imaged. Then this beam is swept across the surface of the object to obtain a terahertz image (in successive horizontal or vertical scans). One can also have an embodiment combining an infrared camera as described above, as well as a flow meter associated with at least one of the elements of the converter 105, in order to determine an absolute value of the heat flow received, this value being a reference for determining each absolute value of the heat flow received at each pixel of the camera.

Of course, the invention is not limited to the embodiments described in the above examples; it extends to other variants. A flow meter based on the Peltier effect was presented in the above examples. Other flow meters can of course be envisaged, particularly a pyrometer. In certain applications, such a flow meter offers the advantage of being faster than a flow meter based on the Peltier effect.

Also, the choice of terasensitive elements used $ZS_{ij}$ can be optimized. "Materials" can be used for which the terahertz absorption is a function of the wavelength, such as liquid crystals in particular, or neutral liquids at concentrations varying in terasensitivity. A multi-spectral detector can thus be realized and a mapping obtained as a function of the power of the radiation and the wavelength.

All these applications are currently envisaged for steady states, but will also be developed for transient states in order to be more effective and increase detection speed.

The invention claimed is:

1. A terahertz analysis device, comprising:
a terahertz source,
a converter for converting terahertz radiation into thermal radiation,
and a thermal detector,
the converter comprising at least one zone sensitive to terahertz radiation, arranged to absorb the terahertz radiation and to convert the absorbed radiation into heat,
wherein the sensitive zone is in proximity to a reference zone, of known absorption capacity,
and wherein the thermal detector is arranged to measure the heat generated by the sensitive zone relative to the heat generated by the reference zone.

2. The device according to claim 1, wherein the thermal detector is adapted to calculate, from said measurement, a temperature difference between the sensitive zone and the reference zone.

3. The device according to claim 2, wherein the heat generated by the reference zone is residual and the temperature difference is indicative of the power of the radiation received by the sensitive zone.

4. The device according to claim 1, wherein the converter comprises a plurality of sensitive elements arranged in an array forming the sensitive zone and separated by boundaries forming the reference zone, and wherein the detector is arranged to measure the heat generated by each sensitive element relative to the heat generated by the reference zone in order to determine a spatial distribution of the terahertz radiation on the converter.

5. The device according to claim 1, wherein the detector comprises at least one infrared sensor, and wherein the device additionally comprises an optical focusing means for focusing an infrared image from the converter on the infrared sensor.

6. The device according to claim 1, wherein the detector comprises at least one heat flow sensor, of the flow meter type.

7. A converter for converting terahertz radiation into thermal radiation, comprising at least one zone sensitive to terahertz radiation, the sensitive zone being arranged to absorb the terahertz radiation and to convert the absorbed radiation into heat, said sensitive zone being in proximity to a reference zone of known absorption capacity for measuring the heat generated by the sensitive zone relative to the heat generated by the reference zone.

8. The converter according to claim 7, wherein the heat generated by the reference zone is residual.

9. The converter according to claim 7, wherein the converter comprises a plurality of sensitive elements arranged in an array forming the sensitive zone, and separated by boundaries forming the reference zone.

10. The converter according to claim 7, wherein the sensitive zone comprises a material in which the terahertz absorption is a function of the wavelength of the terahertz radiation.

11. The converter according to claim 7, wherein the sensitive zone contains at least one material among water, glass, and carbon nanotubes.

12. The converter according to claim 11, wherein the sensitive zone contains at least two terasensitive liquids which can be interchanged by channel means in order to be exposed at the same time to the terahertz radiation with chosen respective propotions.

13. The converter according to claim 7, wherein the sensitive zone contains at least two terasensitive liquids which can be interchanged by channel means in order to be exposed at least alternately to the terahertz radiation.

14. The converter according to claim 7, wherein the sensitive zone and the reference zone are adjacent.

15. The converter according to claim 7, wherein a thermal insulating layer is interposed between the sensitive zone and the reference zone in order to reduce the heat losses from the sensitive zone.

16. The converter according to claim 7, wherein it additionally comprises a heat flow sensor, of the flow meter type, associated with said sensitive zone.

17. A method for terahertz analysis, wherein a converter is provided for converting terahertz radiation into thermal radiation, comprising at least one zone sensitive to terahertz radiation and arranged to absorb the terahertz radiation and convert the absorbed radiation into heat, said sensitive zone being in proximity to a reference zone of known absorption capacity, and the heat generated by the sensitive zone being measured relative to the heat generated by the reference zone.

18. The method according to claim 17, wherein the converter comprises a plurality of sensitive elements arranged in an array forming the sensitive zone, and separated by boundaries forming the reference zone,
wherein the heat generated by each sensitive element is measured relative to the heat generated by the reference zone in order to determine a spatial distribution of the terahertz radiation on the converter.

19. The method according to claim 18, wherein:
an object is placed in the path of terahertz radiation of given power between a source of terahertz radiation and the converter, and
a spatial distribution of the power of the terahertz radiation received at the converter is determined.

20. The method according to claim 19, wherein a first spatial distribution of the power of the terahertz radiation received at the converter is determined, without an object in the path of the radiation, and a second spatial distribution of the power of the terahertz radiation received is determined, with the object in the path of the radiation, and the second distribution is compared to the first distribution.

21. The method according to claim 17, wherein the sensitive zone comprises a material in which the terahertz absorption is a function of the wavelength, and a variation in the wavelength is applied in order to obtain a mapping as a function of the power of the radiation and of the wavelength.

* * * * *